US011651856B2

(12) United States Patent
Bjørkmann et al.

(10) Patent No.: US 11,651,856 B2
(45) Date of Patent: May 16, 2023

(54) METHOD OF CONNECTING A USER DEVICE ANONYMOUSLY TO A REMOTE OPERATOR

(71) Applicants: SWEET TECH AS, Oslo (NO); Kim Rubin, Menlo Park, CA (US)

(72) Inventors: Alexander Bjørkmann, Oslo (NO); Jens Petter Wilhelmsen, Oslo (NO); Nicolay Bang, Oslo (NO); Kim Rubin, Menlo Park, CA (US)

(73) Assignee: Ohdoki AS, Oslo (NO)

( * ) Notice: Subject to any disclaimer, the term of this patent is extended or adjusted under 35 U.S.C. 154(b) by 365 days.

(21) Appl. No.: 17/259,190

(22) PCT Filed: Jul. 26, 2019

(86) PCT No.: PCT/US2019/043602
§ 371 (c)(1),
(2) Date: Jan. 10, 2021

(87) PCT Pub. No.: WO2020/040932
PCT Pub. Date: Feb. 27, 2020

(65) Prior Publication Data
US 2021/0273919 A1 Sep. 2, 2021

Related U.S. Application Data

(60) Provisional application No. 62/721,253, filed on Aug. 22, 2018.

(51) Int. Cl.
*G16H 40/67* (2018.01)
*G16H 20/30* (2018.01)
(Continued)

(52) U.S. Cl.
CPC ............. *G16H 40/67* (2018.01); *A61H 19/32* (2013.01); *G01D 5/00* (2013.01); *G05B 19/042* (2013.01);
(Continued)

(58) Field of Classification Search
CPC ........ G16H 40/67; G16H 20/70; A61H 19/32; H04L 9/0861; H04L 9/088; H04L 63/10;
(Continued)

(56) References Cited

U.S. PATENT DOCUMENTS

2003/0078972 A1* 4/2003 Tapissier ............ H04N 21/6181
348/E7.071
2005/0102244 A1* 5/2005 Dickinson ........... H04L 63/0442
705/74

(Continued)

OTHER PUBLICATIONS

Karabey et al., "A Cryptographic Approach for Secure Client—Server Chat Application using Public Key Infrastructure (PKI)", Dec. 2016, 11th International Conference for Internet Technology and Secured Transactions, pp. 442-446 (Year: 2016).*

(Continued)

*Primary Examiner* — Kenneth W Chang
(74) *Attorney, Agent, or Firm* — Kim Rubin Patent Agent

(57) ABSTRACT

A method of connecting a user device anonymously to a remote operator, via an intermediate anonymizing server is described. In this way, a remote operator may control the device, without the remote operator knowing the identity of the owner or of user of the device. A remote operator might provide medical support or entertainment. The user of the device is provided with a connection key, which is then further given by the user to a desired remote operator. Both the user and the remote operator provide the anonymizing server with the connection key. The anonymizing server opens a chat room uniquely associated with the connection key. Electronic connectivity is provided by forwarding mes-
(Continued)

sages between the user device and the remote operator through the chat room. No other access to the chat room is permitted. The anonymizing server does not store the connection key. No user application is required.

6 Claims, 11 Drawing Sheets

(51) Int. Cl.
| | |
|---|---|
| G16H 80/00 | (2018.01) |
| A61H 19/00 | (2006.01) |
| G01D 5/00 | (2006.01) |
| G05B 19/042 | (2006.01) |
| G06Q 50/26 | (2012.01) |
| H04L 9/08 | (2006.01) |
| H04L 51/046 | (2022.01) |
| H04N 21/43 | (2011.01) |
| H04L 9/40 | (2022.01) |
| G16H 20/70 | (2018.01) |
| G06Q 50/00 | (2012.01) |

(52) U.S. Cl.
CPC ........... *G06Q 50/265* (2013.01); *G16H 20/30* (2018.01); *G16H 80/00* (2018.01); *H04L 9/088* (2013.01); *H04L 9/0861* (2013.01); *H04L 51/046* (2013.01); *H04L 63/0421* (2013.01); *H04L 63/0428* (2013.01); *H04L 63/0876* (2013.01); *H04L 63/10* (2013.01); *H04N 21/4302* (2013.01); *A61H 2201/1207* (2013.01); *A61H 2201/165* (2013.01); *A61H 2201/1664* (2013.01); *A61H 2201/1671* (2013.01); *A61H 2201/5012* (2013.01); *A61H 2201/5025* (2013.01); *A61H 2201/5041* (2013.01); *A61H 2201/5058* (2013.01); *A61H 2201/5064* (2013.01); *A61H 2201/5097* (2013.01); *A61H 2205/087* (2013.01); *G05B 2219/23051* (2013.01); *G06Q 50/01* (2013.01); *G06Q 2220/00* (2013.01); *G16H 20/70* (2018.01)

(58) Field of Classification Search
CPC ....... H04L 63/061; H04L 51/18; G06Q 50/30; G01D 5/00
See application file for complete search history.

(56) References Cited

U.S. PATENT DOCUMENTS

| | | | | |
|---|---|---|---|---|
| 2009/0287920 | A1* | 11/2009 | Fernandez | H04L 63/0428 709/227 |
| 2011/0110364 | A1* | 5/2011 | Fried | G06Q 30/02 370/352 |
| 2012/0331073 | A1* | 12/2012 | Williams | H04L 67/1046 709/206 |
| 2016/0269411 | A1* | 9/2016 | Malachi | H04L 63/0421 |
| 2017/0041263 | A1* | 2/2017 | Shekel | H04L 51/04 |

OTHER PUBLICATIONS

Podolanko et al., "LiLAC: Lightweight Low-Latency Anonymous Chat", Aug. 2017, IEEE Symposium on Privacy-Aware Computing, pp. 141-151 (Year: 2017).*

* cited by examiner

Fig. 3
Fig. 4
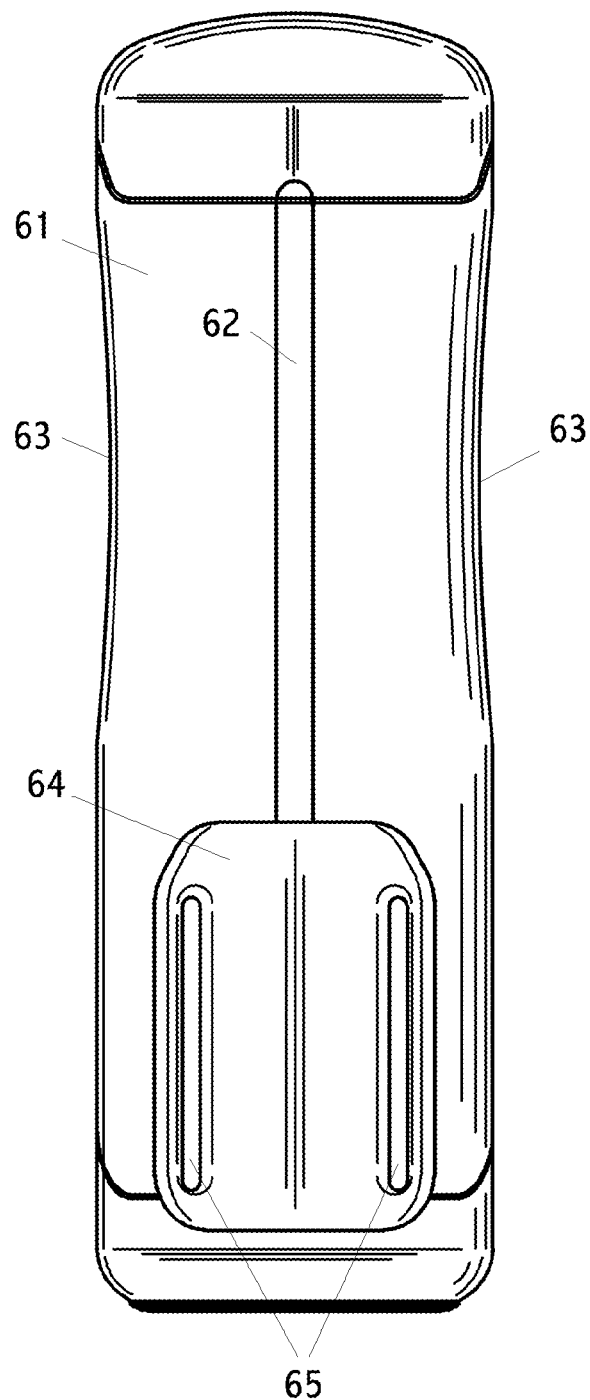
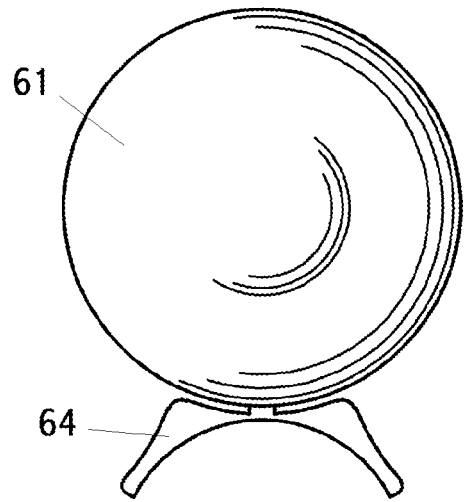

METHOD OF CONNECTING A USER DEVICE ANONYMOUSLY TO A REMOTE OPERATOR

This application claims priority to U.S. Provisional Application 62/721,253 filed 22 Aug. 2018, first named inventor Alexander Bjørkmann.

TECHNICAL FIELD

The technical field of this invention is products and methods for medical and recreational sexual stimulation of a human male, particularly for remote control of such devices.

BACKGROUND

Separated couples often suffer from a lack of physical intimacy. Prior art includes manual stimulation devices and minimally controllable remotely operative devices. Weaknesses of such devices include lack of connectivity options, lack of security, complex interfacing, and a closed software interface. Such prior art devices lack a necessary range of operation and lack of feedback to reasonably simulate real intimate behavior.

Prior art powered male masturbation devices use vibrators or sleeves with linear motion. Motors are brushed motors. Sleeves are internal to the shell of the device. For devices with wireless connectivity, applications are required on a smart phone, which complicates operation and compromises privacy for the user. Use of a smart phone or similar device for control makes third party interfaces to the device either overly complex or impossible. Grips for a hand are on the side of the device. Weaknesses of prior art devices include noisy operation, high power, low reliability, multi-step setup, bulky size, poor ergonomics, lack of privacy, lack of third party access to functionality and inconvenient setup. Lack of connectivity to remote devices prevents the device from being used to provide remote intimacy or remote connection to a caregiver or doctor. Connectivity in prior art devices, if available, requires personal identifying information.

SUMMARY OF THE INVENTION

Embodiments of systems and methods of treatment claimed overcome the weaknesses of prior art.

A system and method of treating lack of intimacy in a patient is described, incorporating an operative penile stimulation device worn by the patient, operated remotely by a caregiver or an electronic process, such a software treatment regimen or a video game. The device provides mechanical linear motion of a driven penile sleeve, external to the body of the device, adjustably fitted to a patient. The stroke length, stroke speed, and stroke position are remotely controllable. Communication between a control device, such as a smart phone, web browser, or application, and the device is through and managed by a server. A caregiver or treatment software connects to a desired patient device solely by the use of a device code, also called a connection key, unique to each device, providing a simple connectivity interface. Such use, in embodiments described herein, enables a private, anonymous, confidential connection between a user and a remote device or remote operator, wherein the connection key is not stored in a server or the manufacturer. Connection keys are stored only devices and by user-selected remote operators. An open interface, such as an API, library or framework, provides for third party control applications, such as treatment software, a video game, virtual reality application, 3D movement recognition, or voice control. One control application may control multiple patient devices. Mechanical motion of the control device may control motion of the patient device.

BRIEF DESCRIPTION OF DRAWINGS

FIG. 3 shows a front view of a device.
FIG. 4 shows a top view of a device.

DETAILED DESCRIPTION OF THE INVENTION

Figure 1:
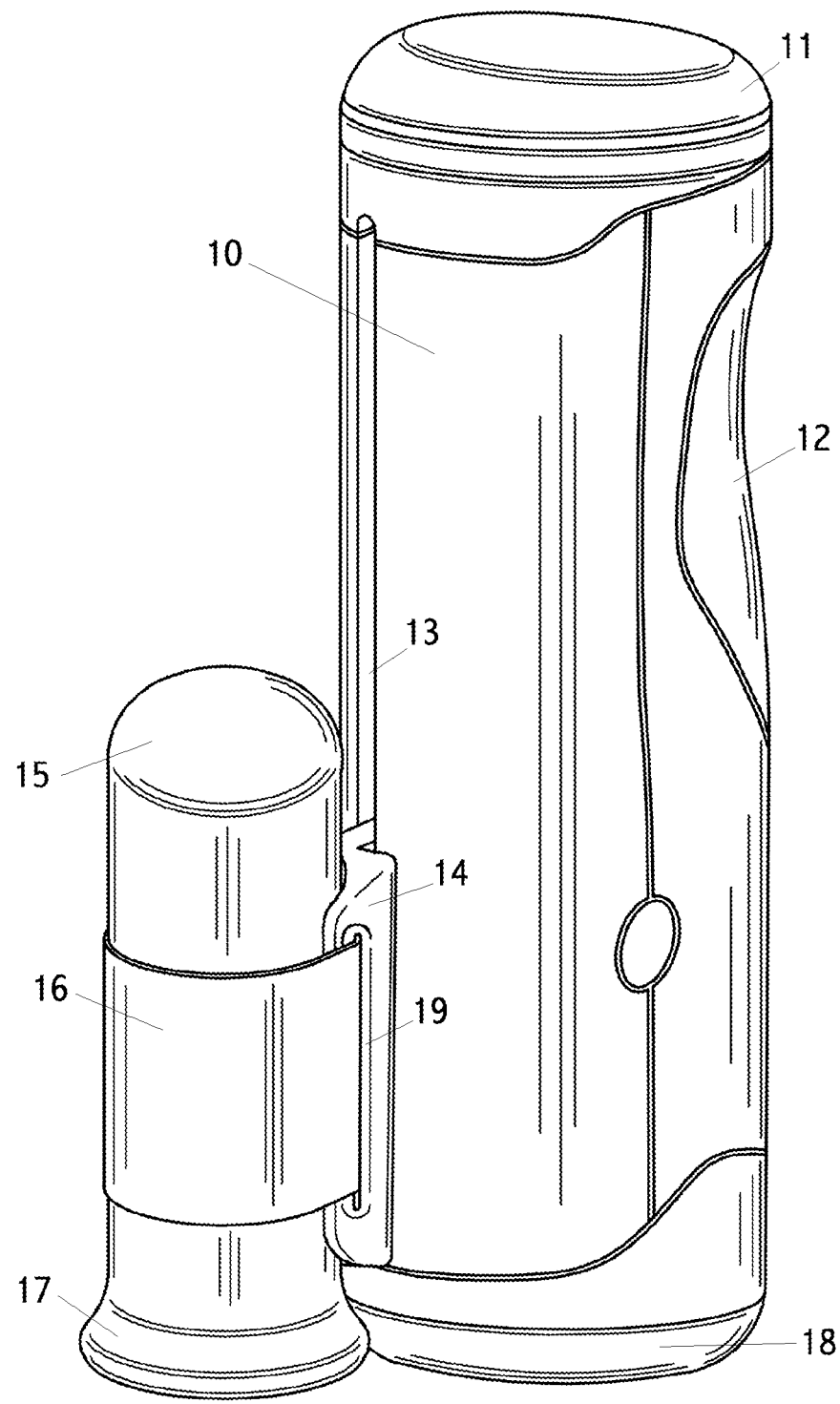
FIG. 1 shows a perspective view of a device.

Scenarios, examples and drawings are non-limiting.

A patient device, a system for providing remote intimacy and a method of treating loss of intimacy are claimed.

System components include but are not limited to one or more patient devices, one or more communication servers, and one or more remote control points, also called remote operators, which may be third party devices or may be part of system or method claims. A key component is an open interface for third party devices.

This invention overcomes weaknesses in the prior art.

Embodiments of this invention include a cylindrical body or shell comprising a primary axis, which is also the axis of the device. The shell contains primary mechanical and electronic components. The shell comprises a slot on one side that is co-linear with the device axis. Internal to the shell is a brushless motor that drives, via a coupler, a lead screw, which is also collinear with the device axis. On the lead screw is a lead screw nut that is driven along the lead screw as the lead screw rotates. The nut is affixed to a slider, which is then driven co-linearly with the device axis. A portion of the slider passes through the slot from the inside of the shell to the outside of the shell. The slider is kept oriented so that it has only one permitted motion in operation by traveling on two alignment, or guide, rods, which that are also co-linear with the axis of the shell. Guide rods may be metal or plastic, and generally have a smooth and low-friction interface with the slider, for quiet, reliable and low-power operation. An external sleeve is removably attached to the external portion of the slider. Use of the device is by a human patient or user, which terms are synonymous herein. Operational buttons are on the outside of the shell, which may be reached by the patient's fingers while the patient's hand holds the distal end of the device, thus permitting one-hand operation. Multiple sensors that detect the location of the slider or nut assure reliable operation that does not require mechanical setup prior to operation.

In operation, a patient first places a removable sleeve over his penis, then connects the sleeve to the external portion of the slider via a strap or other attachment component, with the proximal end of the shell closest to his body and the distal end of the shell held with one hand. Operation of the device, such as speed, stroke length, slider position, and other features, as well as remote connectivity, is controlled by buttons accessible to the fingers of the hand while holding the operative device. The buttons are located in a concave recess in the shell. In operation, the sleeve is driven, via the slider, lead screw nut, lead screw and motor, along the axis of the shaft of the patient's penis. In operation, the device does not requires a smart phone, personal computer, or similar piece of personal electronics comprising a processor, user-interface and communications capability.

Operation includes optional wireless connectivity to a remote operation point, via an intermediate server. Such connectivity does not require any software on, or presence of, a smart phone. No personal data or personal ID is captured or required for remote connectivity. A remote server operates as a data intermediary and anonymizer between the device and a remote operation point. A remote operation point specifies a desired device it wishes to control by a single device ID. Thus IP addresses and other user-identification is not disclosed to an operation point. In addition, no third party smart phone app is necessary, which also preserves patient privacy. The device is adapted to be used as a male masturbation device, which is optionally controlled, monitored or synchronized with a distant, remote operation point. Such connectivity to a remote operation point may provide intimacy with a remote partner, connectivity to a doctor or therapist, or connectivity to a remote device, which might include a video game. Use of an intermediate server not only provides both convenience and privacy, but also permits a single remote operation point to control multiple devices simultaneously.

Turning first to FIG. 1 we see an exemplary view of a patient device, comprising a body or shell 10 and slider 14. The slider 14 connects through the body 10, via one or more slots 13 in the body 10, to an internal platform (see FIG. 2) that is driven linearly up and down. The body, also called a shell, and the device as a whole has a primary axis that is vertical in this Figure and aligned with the length of the body 10. The slider 14 comprises, or is adapted to connect to, a patient sleeve 15, which adjustably fits over the patient's penis with an attachment strap 16, or similar attachment component. In typical use, the patient holds the body 10 of the device, ideally with a single hand holding the distal end 11 of the body 10. When operating, the device drives the slider 14 up and down the patient's penis to provide sexual stimulation. Control of motions of the slider may be provided remotely, such as by the patient's remote partner, a therapist or partner proxy, software, a remote game, or other manual, automated, or intermediate device. Operational buttons on the device for local control are visible in FIG. 2. Buttons are conveniently located in a concave recess 12 in the body 10. Location and positioning of the buttons is novel in that fingers of the same single hand controlling the device may control them. That is, control and typically use of the device may be one-handed; two hands are not required. Buttons may include: on/off, speed up/down, and stroke length increase/decrease. Wireless connectivity may be provided automatically by the on/off buttons or may be controlled separately. Control may be via buttons, touch areas, voice control, motion control such as a wave, motion or position of a hand or other body part, or control via a personal electronic device, such as a smart phone, tablet, or virtual assistant. Size and firmness of fit may be provided via a belt or strap 16, such as a hook and loop fastening strap, elastic, boa, or other adjustment. A removable penile sleeve, such as made out of silicone, EPDM, rubber, neoprene, latex, nitrile, timprene, flexible PVC, thermo-elastic polymers, such as TPE, or other suitable materials, ideally flexible and medically suitable for skin contact. In one embodiment the strap 16 fits through one or more slots in the slider 14. The connecting strap 16 may be removable, permanently attached, single use, or sanitizable, in any combination. Such a strap 16 may be part of the device or provided separately. It may be part of or provided with a sleeve 15. The base 18 of the body 10 is suitable for placing the device, when not in used, on a flat surface. It also is suitable curved so that placement of this proximal end against the body is comfortable. It may be a rigid material such as PVC or may be comprise a softer material, such as silicone or rubber. A sensor (not shown) may be used by the device or via connectivity to identify whether the device is so sitting on a surface or not, such as in use. An alternative sensor for this purpose may be an accelerometer internal to the device. See FIG. 2.

The distal end of the shell 10 is curved, with no discontinuities between the distal end 11 of the shell and the sides of the shell, permitting the shell to be comfortably held using a natural hand location and position. The shell, as assembled by the manufacturer, sold, shipped and used, is a complete unit, requiring no assembly or disassembly by the patient. The sleeve 15 is easy attached and removed, such as by using a strap 16, which in some embodiments passes through retention slots visible in the external portion of the slider 14. The strap 16 may comprise hook-and-loop surfaces for fast, convenient, adjustable attachment and firmness of the sleeve against the patient's penis. Other attachment methods include but are not limited to: magnets, snaps, slides, screws, catches, pins, zippers, quarter-turn fasteners, removable adhesives, and the like. Sleeves may be made of different materials in order to provide different feel, compatibility with different lubricants, ease of cleaning and cleaning options, different sizes, internal shape, appearance, longevity, and the like.

In use, after fitting the sleeve 15 to himself, and then attaching the sleeve 15 to the sleeve retention portion of the slider 14, the shell 10 is held in one hand, with the palm against the distal top cap 11, and that same hand activates power and optionally speed and other features via buttons on surface 12, without removing his hand from the distal end of the sleeve. In an embodiment shown, the shell 10 has a concave recess 12. A slot 13 in the shell permits an internal lead screw to drive a slider 14, which extends through the slot 13. A sleeve retention portion or concave shape of the slider 14 is external to the shell 10. Buttons may be any combination of electronics and sensors that detect a finger or pressure. That is, they may be "touch controls," rather than mechanical controls. 19 shows a slot for a sleeve-retention band or strap. There are many ways to removably attach the sleeve or a sleeve strap to the device, including hook-and-loop fasteners, a buckle, snaps, zippers, static electricity, friction, wax, and removable glue, for example. Optional visual or audible indicators are not shown in the Figure. A visible indicator may be in the recess 12, for example, or illuminate the sleeve, such as being in or proximal to the slider 14.

Figure 2:
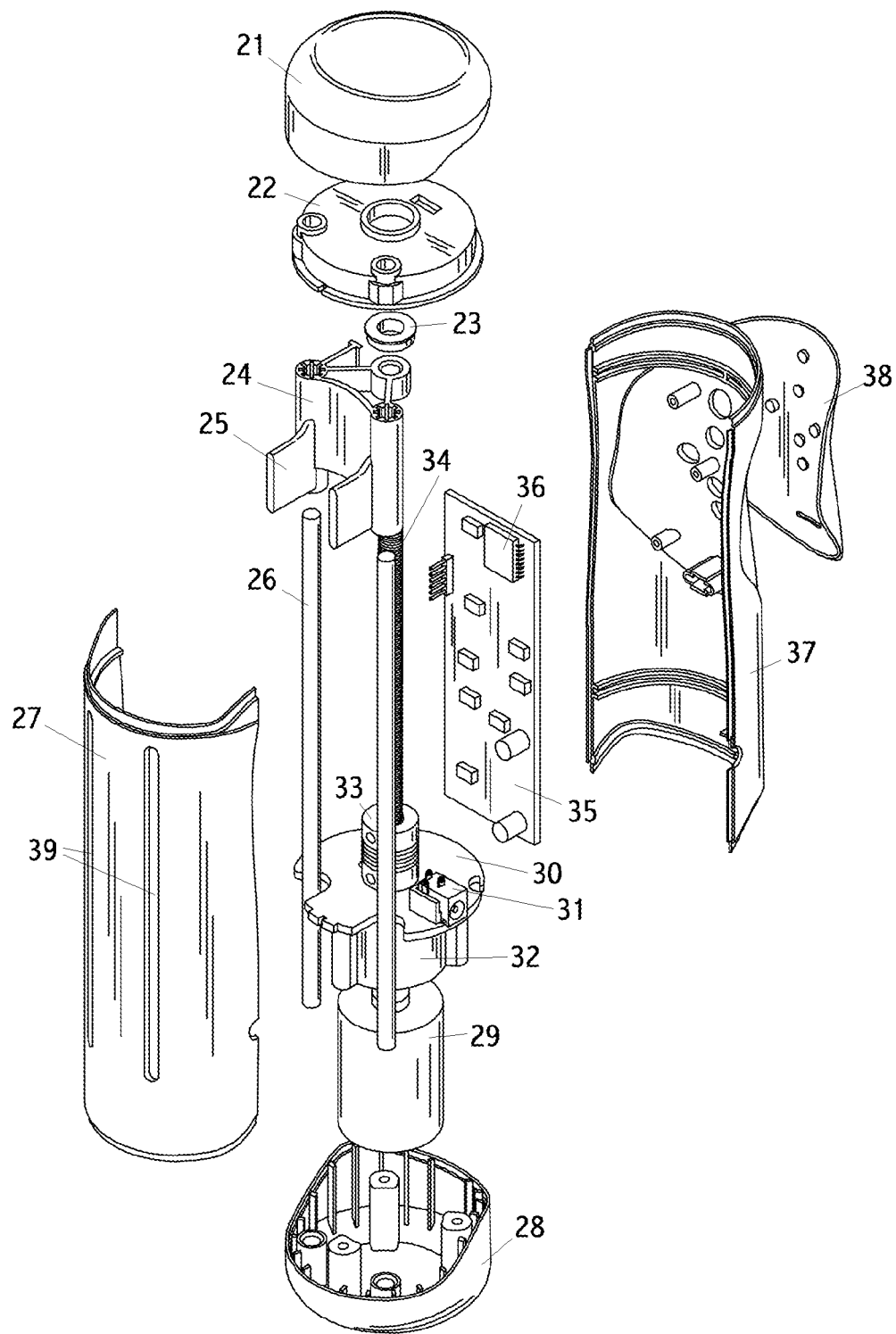
FIG. 2 shows an exploded view of a device.

Turning now to FIG. 2, we see an exemplary exploded view of the body and shell and components of the body and interior to the shell. In this Figure, a sleeve and sleeve attachment strap are not shown. Elements include: A distal or upper body cap 21; a distal mechanical terminator 22; lead screw bearing 23; slider 24; one or more slider arms 25, which penetrate via one or more slots 39; one or more guide rods 26 which pass through at least a portion of the slider to maintain slider alignment. Elements of or elements proximal to the slider 24 include one or more slider arms 25, a lead screw nut not shown. A sleeve retainer, 14 in FIG. 1 and not shown in this Figure, may be attached or removably attached to the slider arms 25. Slider arms 25 may comprise a slot, such as 19 in FIG. 1, or other element with which to attach a strap such as 16. In another embodiment, an additional retention element, not shown, may be located between the slider arms 25 and a strap, such as 16. Such an element may be considered part of the slider arms 15 or may be considered part of a sleeve retainer. Rotation of a lead screw 34 causes the slider 24 to move co-axially with the shell. In other embodiments, the slider 24 may be aligned by another device or method, such as by one or more slots 39. Primary motion is provided by a motor 29 connected operationally to a lead screw 34 via an optional mechanical coupler 33. In one embodiment, the lead screw 34 is connected directly to, or is part of, the rotor shaft of motor 29. Rotation of the lead screw 34 by the motor causes the slider 25, via a lead screw bearing 23, directly or indirectly affixed to the slider 25, causes the slider to move up and down in the body of the device, with the external arm or arms 25 of the slider connecting to a sleeve strap, in FIG. 1. The slider arm or arms 25 penetrate one or more slots 39 in a portion or side 27 of the body. Elements top cap 21, bottom cap 28, left shell portion 27, and right shell portion 37 make up the primary elements of the exterior of the body or shell of the device. Keys 38 may be implemented in different embodiments as a flexible key component 38 as shown, or individual keys, or a touch interface. In the embodiment shown, molded keys in monolithic, flexible sheet 38 penetrate holes in shell portion 37 to interact operatively with key sensors (not shown) on the backside of the printed circuit board (PCB) 35. The PCB comprises one or more circuit boards to hold electronics, and optionally a programmable processor, sensors, lights, and switches, and a wireless communication interface. 30 is a lower platform providing support of mechanical components as shown. 31 is a connection to an external power source, such as a low-voltage plug, USB-C connector, or similar. End-of-motion sensors are not explicitly shown in this Figure.

They may be located on the circuit board 35. An end-of-motion sensor, which may be a mechanical switch, proximity sensor, magnetic switch or sensor, optical sensor, and the like. It detects a lower limit of the slider 24 at the base (proximal end) of the lead screw 34. Similarly, there is an end-of-motion sensor, not shown, at the upper (distal end) of the lead screw 34. 32 is a portion of the lower platform or motor base, 30. A lead screw "bearing nut" is not shown in this Figure. In other embodiments, the bearing nut may comprise only a bearing, or only a nut, or it may be missing entirely. It may be affixed to or inside the slider 24.

A processor or microcontroller 36, which may be one or more chips, comprises non-volatiles program memory, random access memory (RAM), and optionally reprogrammable non-volatile memory such as FLASH, EPROM or EEPROM. Such reprogrammable holds a unique device ID.

Continuing with FIG. 2, a circuit board 35 contains primary electronic components, such as a power supply, optional batteries, one or more processors 36, wireless communication chips and antennas, motor drive electronics, end-of-motion sensors, such as 31, optional voice input and/or voice output, button inputs and light outputs. Electrical connections for power, or for a battery charger, and associated connectors, are not shown.

One embodiment of electronics and mechanics inside the shell comprises motion sensors that may indicate end of travel, location of the slider 24, travel speed, or rotational position or speed of the motor 29 or lead screw 34. An exemplary sensor is shown 31. One or more sensors may be inside the motor housing 29. Sensors may be infrared (IR) sensors, Hall effect sensors, or another sensor technology in any combination. In general, sensors may be mechanical, proximity, inductive, capacitive, RF (such as RF ID), optical, IR, audio, magnetic, Hall effect, or another sensor technology. Typically, there are multiple places where sensors may be placed. For example, any sensor that detects slider position or angular motor position, such as might be used to determine motor and therefore slider speed, may be place almost anywhere on or proximal to moving parts, including inside the motor, on the motor shaft, inside the motor housing, on the lead screen, on the guide rods, on the rotational coupler, on the circuit board. Each sensor may comprise a pair of components, or only a single component. Note a patient or a remote caregiver or device may adjust the stroke length, stroke speed, or other operational parameters independent of the fixed, predetermined location of any sensors or use of operational buttons. In one embodiment, one or more over-temperature sensors may be used to detect motor overheating or another operational defect. Such sensors may be located in or on the motor 29 or on the circuit board 35.

Turning now to FIGS. 3 and 4, we see respectively a front view and top view of embodiments, showing the body, without a sleeve attached. Note that the term, "body," generally refers to the primary portion of the device without the sleeve; while the term, "shell," generally refers to the enclosure, without the interior electronic and mechanical components. However, depending on context, the term, "body," may refer to the shell portion of the device. At the top of FIG. 3 is the distal end of the shell or device 61. 62 is a slot, through which an arm of the slider 64 penetrates. In use the slider is connected to a sleeve (not shown) and moves up and down along the primary axis of the device, through the shell. An embodiment has one or more concave regions 63. These provide enhanced grip, ability of the users to easily sense rotational angle of the device, and which hold recessed buttons, shown in FIG. 2. The slider 64 comprises, in some embodiments one, two or more slots 65, through which a belt or strap, described elsewhere herein, passes, such that the belt of strap comfortably and conveniently holds a sleeve. The belt or strap is adjustable to assure an appropriate fit for a range of users. In FIG. 4, we see a top view of the device 61, and a top view of the slider 64.

An exemplary embodiment comprises operational buttons and visual indicators, such as lights. Indicators may be audible or haptic, in any combination. Note that in one embodiment buttons are located in the smooth concave recess 12 in FIG. 1. One button, not shown, may implement a power on/off function. Two pairs of opposing buttons may implement speed of stroke up/down function, and a stroke length increase/decrease function. An embodiment may comprise one or more multicolor status indicators, which may indicate such states as on, or connected to a remote server, or connected to a remote operation point. It might also indicate a master/slave or slave/master relationship between this device and the remote operation point. Colors may include, besides off: red, green, blue, white, in any combination, including alternate color blinking or alternate on/off blinking. Such one or more indicator may be located anywhere on the device, such as next to or behind buttons, not shown. An optional light or other visual indicator may be located in a recess 63. A visual indicator maybe inside the device, shining through a transparent or translucent portion, or through an opening, Such an indictor may cause sleeve 15 to illuminate. A button or combination of buttons, or other input to the device, may initiate, confirm, or terminate remote operation.

Figure 5:
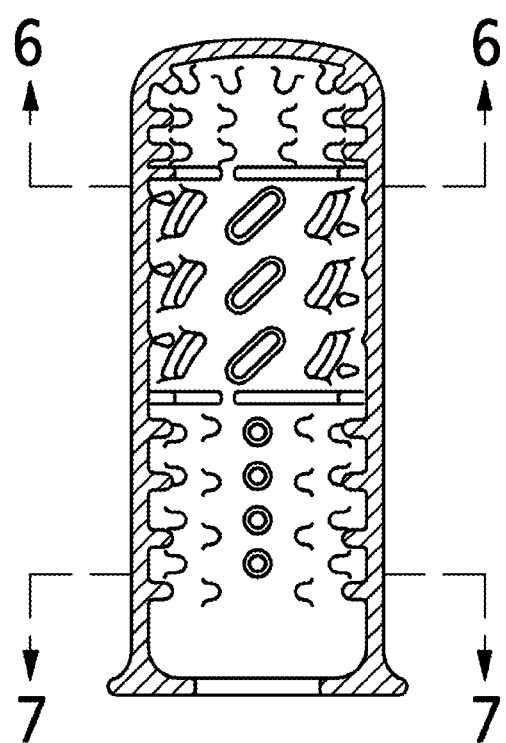
FIG. 5 shows a vertical cross section of a sleeve.
Figure 6:
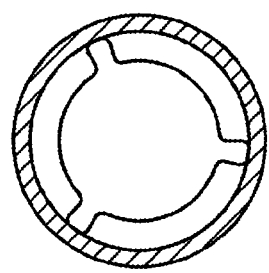
FIG. 6 shows a first horizontal cross section of a sleeve.
Figure 7:
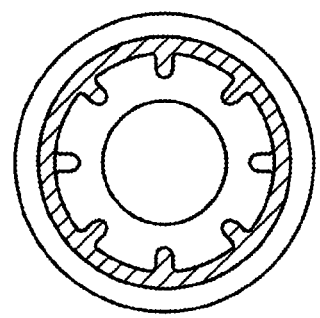
FIG. 7 shows a second horizontal cross section of a sleeve.

Turning now to FIGS. 5, 6 and 7, we see one embodiment of a sleeve, which may be made of silicone, or other flexible material as described elsewhere herein. FIG. 5 shows a vertical cross-section where various internal projections, or nubs are visible. These nubs provide a firm grip on a user's penis and also provide sexual stimulation during use. In this view, the sleeve has an opening at the bottom and is closed at the top. Typically, sleeves are washable, sterilizable, and re-usable, but sleeves may be single use. Different sleeves may be used depending on the desire and fit desired by a user. FIG. 5 shows two horizontal cross section lines 6-6 and 7-7. These cross sections are shown respectively in FIGS. 6 and 7. In FIG. 7, cross sections of nubs are clearly visible. Note that the opening at the bottom of FIG. 5 and visible as the inner circle in FIG. 7 is smaller in diameter than most of the interior of the sleeve. This assures a firm fit.

Figure 8:
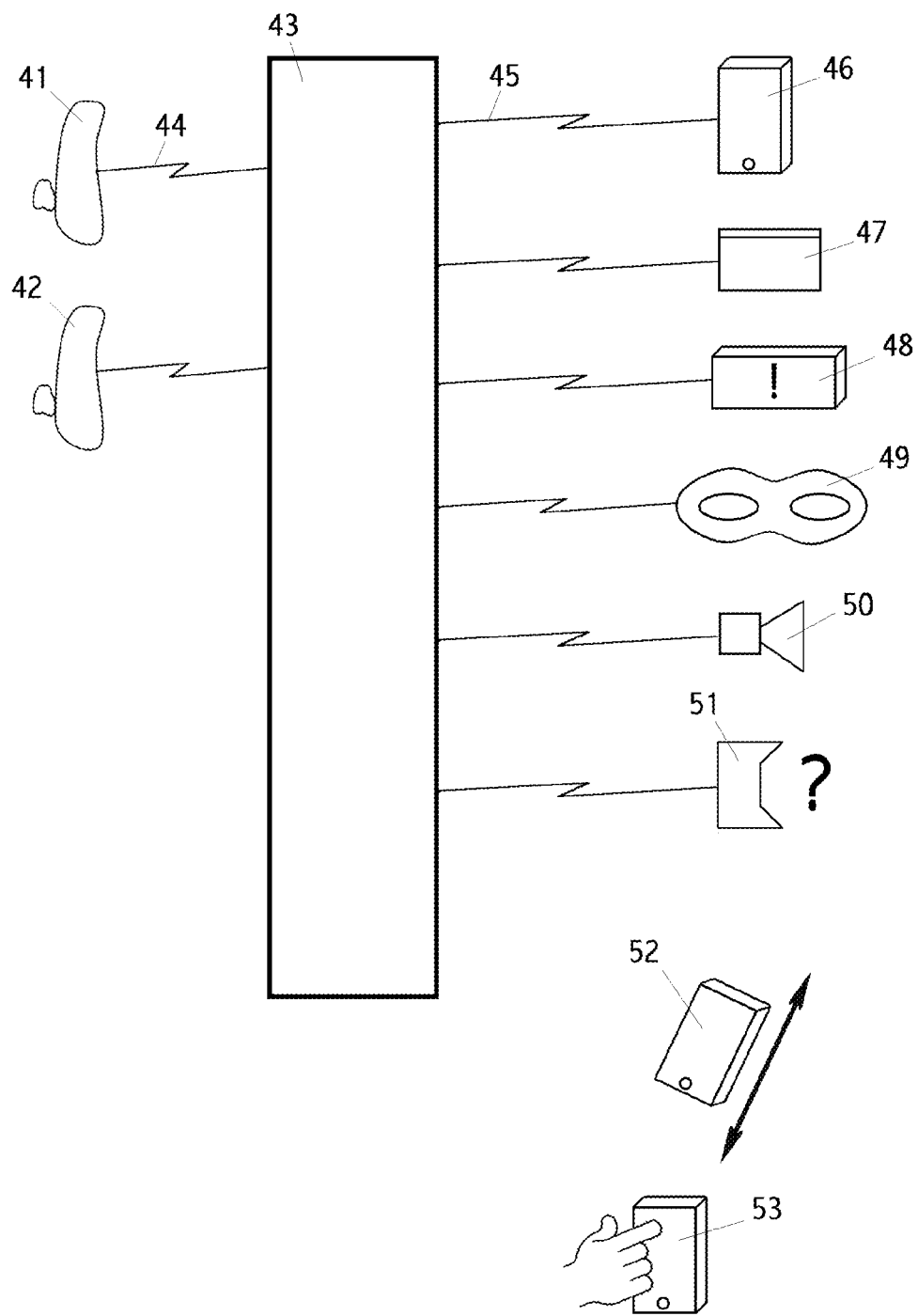
FIG. 8 shows a range of connectivity options of a device.

Turning now to FIG. 8, we see elements of an embodiment of a system and parts of a method of treatment. One or more communication servers are shown 43. Such a server provides communication functions, security, user interface, data storage and management, device and user setup and registration. A novelty of embodiments is the use of the server as an intermediate between a remote control and the patient device. Prior art devices use a direct connection, such as the internet. The use of an intermediate server 43 provides simplified access to both patients and remote control people or devices, better security, and the ability to have more than one patient device and more than remote device, in configurations other than prior art one-to-one configurations. For example, one remote device, such as a therapist or video game, may control more than one patient device. Or, more than one remote device may control a single patient device. A remote device may be a remote operator or a remote device operator.

FIG. 8 shows two exemplary patient devices, 41 and 42. 44 shows an exemplary communications link, which may in turn comprise any number of sub-links and technologies, such a Bluetooth, WiFi, IR, cellular voice or data, internet, or other wired or wireless, public or provide, sub-links. For example, a patient device 41 might communicate directly via Bluetooth or WiFi to a patient phone (not shown), which then communicates via cellular data to the internet, which in turn connects to server 43. In general, all communication links are two-way. 45 shows a similar generalized communication link between the server 43 and exemplary remote devices 46 through 51.

A novelty of embodiments is the range of remote devices that may control one or more patient device. Shown are a smart phone or tablet 46, and web browser 47, a video game 48, an virtual or augmented reality device 49, a camera or 3D camera 50, and an open interface 51. Device 50, identified generically but not specifically as a camera, may be used to track, translate and interface observed movement, without the need for a remote control person or device to be mechanically connected. For example, hand motions, body motions, or visual reading of lips may be used to control the patient device. A device such as Microsoft® Kinect® has such device capabilities. A device such as an Apple iPhone X has such hardware capabilities. A device such as 50 may control more than one patient device, 41 and 42, at the same time, either synchronized or independently.

Of particular novelty is an open interface 51, which may be an Application Programmer Interface (API), a software library, a software framework, XML interface, or other known mechanisms for documenting and implementing functionality for third party; devices. This permits third party developers to offer their own system-level functionality. For example, a treatment center may wish to provide its own care providers or software. As another example, a prison may wish to provide their own security and monitoring of interfaces to patients. As yet another example, a video game may provide game actions, characters or elements linked to patient devices. As yet another example, a resort may wish to offer guests access to patient devices as part of a resort package.

FIG. 8 shows, 52, one method of remote control. Here, physical motion of a device such as a smart phone is translated directly into motion of a slider on a patient device. Yet another method of control using a smart phone, tablet or touch screen is shown in 53, where finger motion(s) translates into one patient device characteristics. Typical characteristics include stroke speed, stroke length, and slider position. Note that communication may be bidirectional and include voice, sound, sound effects or haptics, in any combination. Such bidirectional communication permits advanced features, such as a patient verbally requesting an action from a character in a video game, and that character providing both action and sound effects back to the patient device.

In one embodiment or operating mode, the device is easily used as a stand-alone device with no external connectivity. In other embodiments the device uses a power cord, not shown. Devices may be powered by light, "solar powered," or use a primary battery. Devices may be charged with a connector-free charger. In another embodiment, the device is controlled partially or wholly by an electronic device in control of the user, such as a smart phone or remoter controller, such as 52 or 53.

Figure 9:
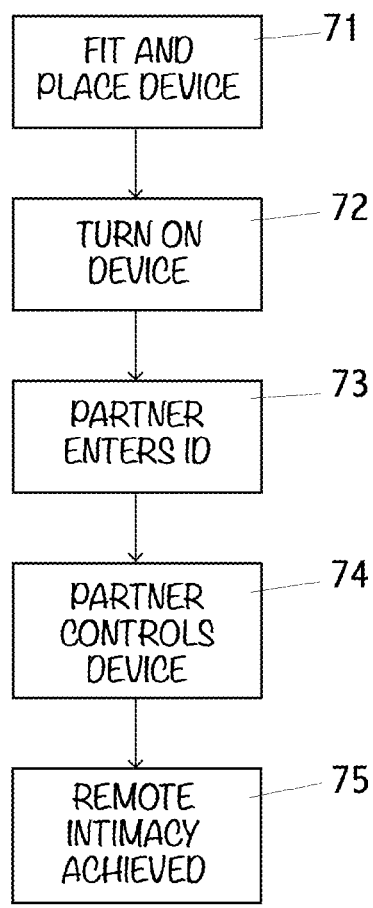
FIG. 9 shows method flow of device usage with a remote partner.

Turning now to FIG. 9, we see one embodiment of flow of a method of treatment for lack of intimacy. In 71, a patient adjusts and fits a penile sleeve connected to the slider of a patient device to his penis. In 72, he turns on his device. In one embodiment he then presses a button enabling remote interface, which might be labeled, "communicate," "Wi-Fi," "Bluetooth," "pair," "remote," "partner," or similar. Note that a variety of communications protocols may be used, as discussed elsewhere herein. Such connection is generally initiated explicitly by a user to assure privacy. Some embodiments pair automatically, such as with a local smart phone, if such pairing has previously been setup by the users. Whether manually or automatically the device connects automatically to a server 43 (in FIG. 8). In 73, a remote partner or device enters a device ID, which may be a non-limiting 4 to 16-character text string, into an interface device (such as 46 through 51 in FIG. 8). An important novelty of embodiments is the use solely of such a device ID for connectivity, rather than prior art requirements of a user name, password, and other parameters. Note that no such identification of any kind is required of the patient, such as in or around steps 71 and 72. Once connected, the device automatically connects to the server 43 and identifies itself uniquely. Thus, the sole, "data entry," required in a system or method embodiment, is entry of such a device ID text string by a remote person or device, once original or one-time device setup or provisioning is completed. In step 74 the remote person, device or software controls the patient device. In this way, embodiments of the system or method successfully treat loss of intimacy due to a partner being remote or non-existent. Such systems and methods may also be used to treat sexual dysfunction, including the use of remote or automated therapists.

Turning now to FIGS. 10A, 10B, 10C and 10D, we see schematic arrangements of devices and communication pathways of various system embodiments. In all four Figures, the same icon refers to the same device, device class, object, service or communication. icon 81 represents a person, typically a patient or user. Icon 82 represents a physical embodiments of a device of this invention. Icon 83 represents a computer, display device, or user interface, including input, output, computation and memory capabilities in any combination. Icon 84 represents a communication device, such as a router, Wi-Fi access point, modem, cellular data device, virtual assistant, or other physical device capability of communicating wirelessly. Icon 85 represents a server, which may be a distributed device or capability. Devices represented by icons 83, 84, and 85 may be local, distributed, embedded, or virtual, and may be part of another device or themselves include another device or capability. Icon 86 represents a medical provider, which may be a human, such as a doctor, nurse or therapists, or software performing a medical function, or a device performing a medical or entertainment function.

In FIGS. 10A, 10B, 10C and 10D, we see four sequential steps respectively, in one embodiment, of how a remote connection is made between the device and a remote server. Five icons are shown, 81, 82, 83, 84, and 85, representing respectively: a patient 81 using a device; an embodiment of the device 82; an electronic user interface device 83 accessible to the patient, such as a PC, capable of running a web browser accessible to the patient and connected to a remote server; a Wi-Fi access point, Bluetooth interface, router or modem 84 within range of the device and connected to a network such as the internet (not shown); and a remote server 85 connected to the network. Icons are replicated in steps described without being repeatedly labeled. Note that a device such as a smart phone is not shown, and is not required for either setup or operation. However, the electronic user interface device 83 may be or comprise a smart phone or tablet. An advantage of embodiment is that they do not need to download an app, which typically compromises patient privacy. The electronic user interface device 83 may use or comprise a standard web browser to access the server and a remote caregiver or application, without requiring or exposing any patient ID. A remote caregiver or remote operation point is not shown.

Figure 10A:
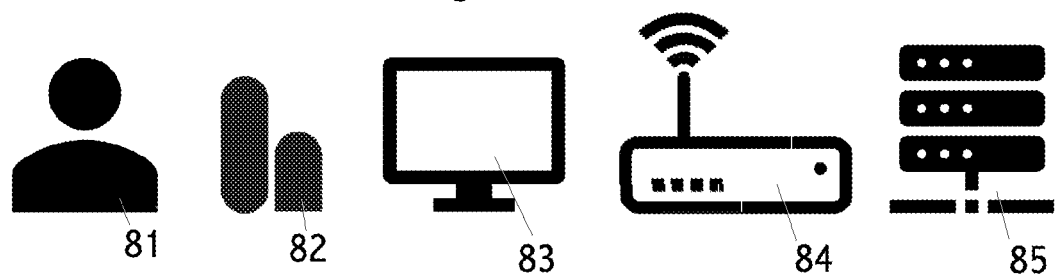
FIG. 10A shows a first configuration of remote connectivity components.

In one operation scenario, using the devices represented by the icons in FIG. 10A, the patient 81 turns on power of the device 82. The user may press a connectivity button on the device 82 to initiate connectivity or such connectivity may initiate automatically. The device 82 accesses the remote server 85 via the local access point 64 and then optionally through the user interface device 83.

Figure 10B:
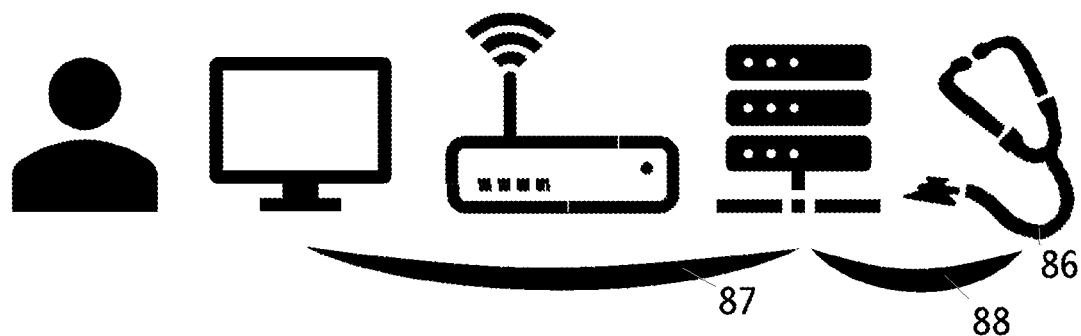
FIG. 10B shows a first data flow of remote connectivity.

FIG. 10B show the patient selecting a remote operation point 86 by using a web browser to enter a connection key, also called a connection code, which uniquely identifies the remote operation point 86. Connection to the selected remote operation point is via the remote server 85, which helps protect user privacy; for example, any internet address (IP) available to the server is not passed on to the remote operation point. Similarly, the server may also block or disguise an ID of a remote operation point. In some embodiments, the server may select a remote operation point. Connection keys should be resistant to hacking and should contain ID related information. They may be views as a combination of an ID (e.g., a URL or login name) and a password. Such a combination simplifies operation for the patient and also assists in protecting privacy. Examples of a connection key are "IGdv3Vuxee3Tpd" or "ˆ8JHpˆc@c%8si]." The remote server may provide a connection key. Ideally such connection keys are also unique to patient. That is, a single connection key is unique for each patient and remote operation point pair. Connection between the patient and the remote service is shown schematically as 87. Connection between the remote server and the remote operation point is shown schematically as 88. Note that in both cases, typically, intermediate communication devices are needed to implement a connection. Connection 87 uses a connection key. Connection 88 may also use a connection key, different than that use for link 87; or a conventional URL or IP address may be used. WebSocket protocols may be used, although other operational protocols may also be used. See elsewhere herein for connectivity details and steps. Connection keys and associates services may be distributed to more than one device or service; that is, element 86 may be distributed, or comprise more than one service or connection to a server.

Figure 10C:
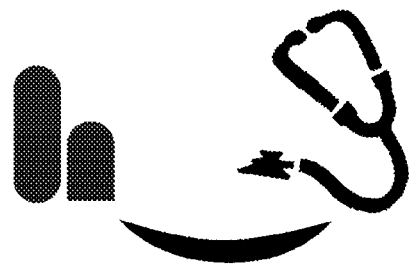
FIG. 10C shows a first effective remote device control.

FIG. 10C shows an embodiment of a logical and effective connection between the device and the remote operation point, as a result of previous steps.

Figure 10D:
FIG. 10D shows a second effective remote device control.

FIG. 10D shows another embodiment. Here, the patient uses the electronic user interface device, such as a web browser, to select options or services desired from the remote operation point. The patient also wears the device. FIG. 10D is schematic.

Another embodiment of connectivity and remote control in operation, following a one-time setup, is described in the following scenario. The patient or a remote caregiver uses a user interface device to go to a website that provides a service compatible with the device. The website, under the direction of the user or caregiver, and a connection key, connects to the server. The server then responsively created a logical, "room." The patent then powers up the device and establishes device connectivity, such as by pressing a connectivity button. The device then connects using Wi-Fi, Bluetooth or another wireless protocol, using the local access point, via a wide area network such as the internet, to the server's "room," using its own connection key. This process established end-to-end connectivity between the device and the compatible service, with the server as an intermediate communication device. The server may act only as a forwarding conduit for information, or it may provide, "store and forward" capability, or it may provide either or both "push" and "subscribe" services; or it may provide logical translation services, or it may provide additional services related to the device. It may provide storage or statistical gathering. It may provide recommendations. It may provide debugging steps. It may be a conduit for customer support or on-line help. It may provide encryption or other privacy features. It may provide redundancy, such as offering alternative remote services. It may provide a menu of service options. It may maintain or provide billing or usage information. It may assure privacy via randomization, anonymity, encryption, or deletion of all identifying information. The server may connect to third party services, not shown in FIGS. 10A through 10D. The server may provide "one-to-one" connectivity; "one-to-many" connectivity, "many-to-one connectivity," or "many-to-many" connectivity. For example, one caregiver or video game or video movie may connect to multiple device and multiple patients. As another example, a patient may connect to both a human caregiver or intimate partner, and to a video movie or game. "Rooms" may be provided by the server at any point in a communication setup sequence. For example, empty rooms may be pre-provisioned; a room may be created upon first communication or request by either a patient or remote operation point; a room may be created only when both the patient and remote operation point are connected or in the process of being connected to the server.

The server may provide analysis and generate responsive commands to one or the other communication end. Exemplary services of a device, system and method include without limitation: video, with or without synchronization; a movie comprising adult or non-adult content; chat using a human or non-human, or combination of chat service. In one scenario, a movie is analyzed to determine effective speed and stroke length as depicted in the movie, and then responsive commands sent to the device, permitting the device to accurately mimic the action in the video. In another scenario, motions of the device are translated by the server and provided to a video source, or to a local, buffered copy of the remote video, or an electronic video game, such that the video appears to be synchronized to the operation of the device. Audio may be synchronized in similar fashions. Note that a service provide by the server may include compensation for communication delay, which may include predictive behavior determination. Operation in such scenarios may be modified in real time by the patient, caregiver, or remote operation point, or website. In one scenario, a third party website, video source, video game, or caregiver may provide data, instructions or recommendation to both the patient and the remote operation point.

There are multiple embodiments for connection keys. Connection keys are fundamental to novel embodiments. A connection key may be related to a connection between a patient/device and the server. A separate connection keys may be related to a connection between the server and a remote operation point. A single connection keys may be related to an end-to-end connection between the patient/device and a remote operation point. Connection keys may be predetermined, rarely changed, such as a traditional login or password. Connection key may be single-use, and generated for each connectivity session. Connection keys may be generated or provided, or both, by any source, including either internal to device, systems, methods and remote operation points, or a server, or from a third party. One or more connection key may be provided with or programmed into a device as delivered to a patient. Note that this feature is particularly convenient for a patient, and is specifically claimed as an embodiment. Coupons, vouchers or advertisements may be associated with connection keys.

Note that in all scenarios and descriptions above no smart phone downloaded app is required, other than a optionally a non-built-in browser in some embodiments, and no patient identifying information is disclosed to any third party, including remote operation points. See elsewhere herein for descriptions of connectivity and associated elements.

A one-time setup is required prior to the operational sequences and results described above. Assistance in such setup may be via a paper document, steps on a website, instructions provide by the remote server 85, or instructions provided by the remote operation point 86, in any combination. Such one-time setup described herein does not include conventional setup of a user interface device 83, a Wi-Fi access point 84, or any necessary intermediate connections. The device 82 needs to know the Wi-Fi network name and password; or the equivalent for Bluetooth, BLE connection a cellular data connection, and the like. Such connectivity may be provided by or include an initial connection between a new device 82 and the user Wi-Fi access point 84. Connection keys may be stored in the user interface device 83, or not stored, requiring entry or re-entry by the patient each time. Devices may be provided with, such as configured prior to delivery to the patient, an initial connection key to assist the patient in one-time setup and in first-time use. See elsewhere herein for additional details and embodiments of connectivity and related devices and elements.

Figure 11:
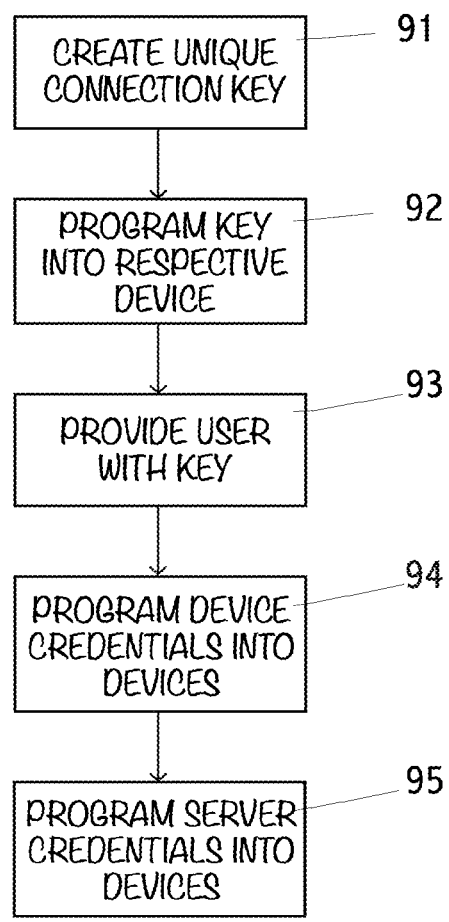
FIG. 11 shows a method of a manufacturer provisioning devices.

Turning now to FIG. 11 we see one embodiment of a device manufacturer, or an entity so authorized by the manufacturer to provision, configure or program each device with a unique connection key. In step 91 the manufacturer creates or acquires a unique connection key. Such a key may be a sequence of printable symbols, based on a random, pseudo-random, or other method of key generation. A key may be binary. Ideally, such a key is long enough to discourage hacking and short enough to provide convenience to the user. For example, a key might comprise a string of 3 to 32 printable characters. In step 92 the manufacturer programs the unique connection key into each respective device. The unique connection key is now uniquely associated with exactly one device. In step 93 the manufacturer provides the user with the unique connection key. Such step may be performed by including the key on paper in a box comprising the product, or electronically to a user. A key may be associated with a serial number or may be a serial number. Although the key is typically programmed into a device by the manufacturer, a distributor, or a service provider prior to sale, such programming may occur after a device sale. In some embodiments, such a key is not provided with a device, but rather is generated or selected by a user following steps in FIG. 14. Note that following step 92 or 93, the manufacturer may delete any record of the key from step 91. In this way, privacy is assured to a user because the only copy of the connection key is in his device. The user may provide his connection key to user-selected remote operators. This method substantially reduces the chance that a key is misused, a key is discovered via hacking, or an association between the key and a user becomes public knowledge or in fact becomes known to anyone other than the user. Although a remote operator so provided with the connection key may connect to a user's device, as described elsewhere herein, the remote operator does not know the identity of a user or person associated with the device or unique connection key. Of course, a user may choose to identify himself to the manufacturer, a remote operator, or other third party.

Figure 14:
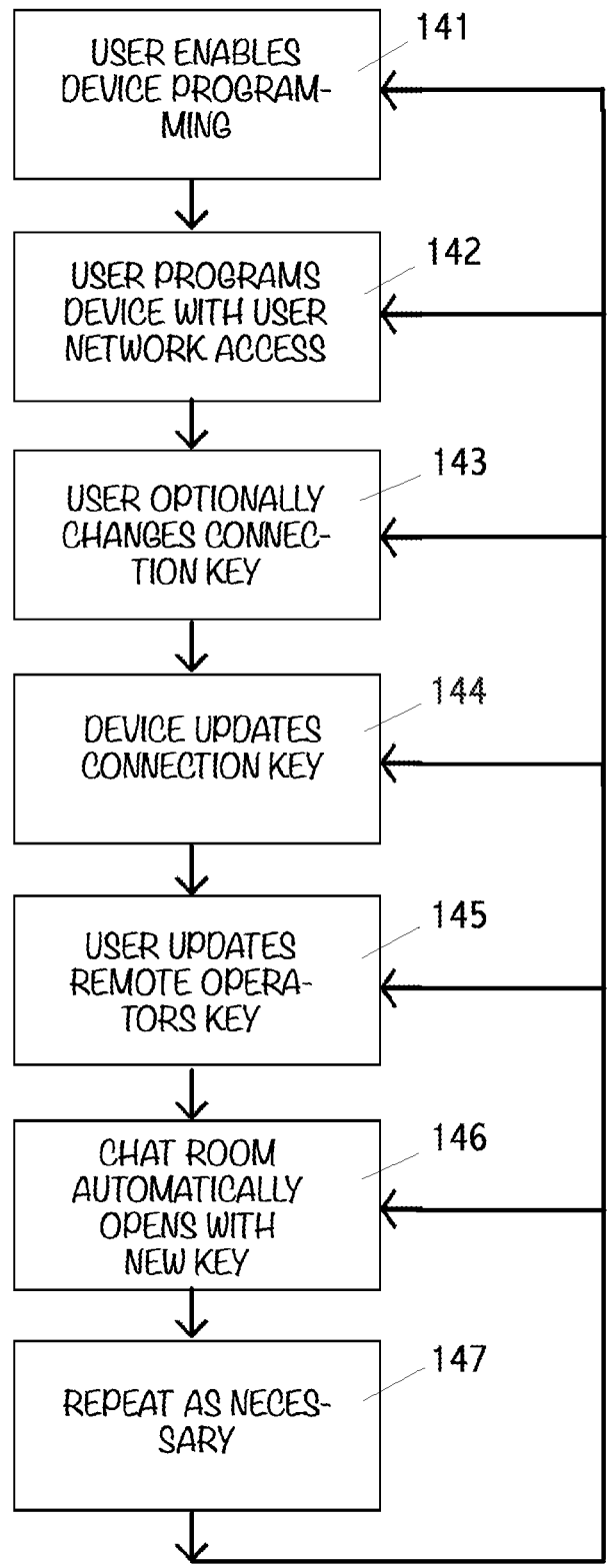
FIG. 14 shows a method of updating a connection key.

Continuing with FIG. 11, in step 94, the manufacturer programs multiple devices with access credentials to create a local, private network, to enable steps 141 and 142 in FIG. 14. Such access may enable a device to be a Wi-Fi access point and host a browser server, so that a user may use an appropriately enabled personal electronic device to configure a device, using the local, private network, such as shown in FIG. 14, for example. In step 95, the manufacturer programs multiple devices with network access and server access credential to enable the device to access the manufacturer's remote server. Step 95 may comprise programming a URL, IP address, and optionally a password, so that a device may use the internet to access the server via the user's internet connected local router or access point.

Continuing with FIG. 11, note that typically the private, local network created or managed by the device, using credentials from step 94, is a different network than the user's typical local network, typically provided by the internet connected local or router as discussed above. For example, the later network may be the user's "home network," frequently always on. While, the former local network is activated once, for a brief period of time, for the purpose of the user programming the device, such in step 142 in FIG. 14.

Figure 12:
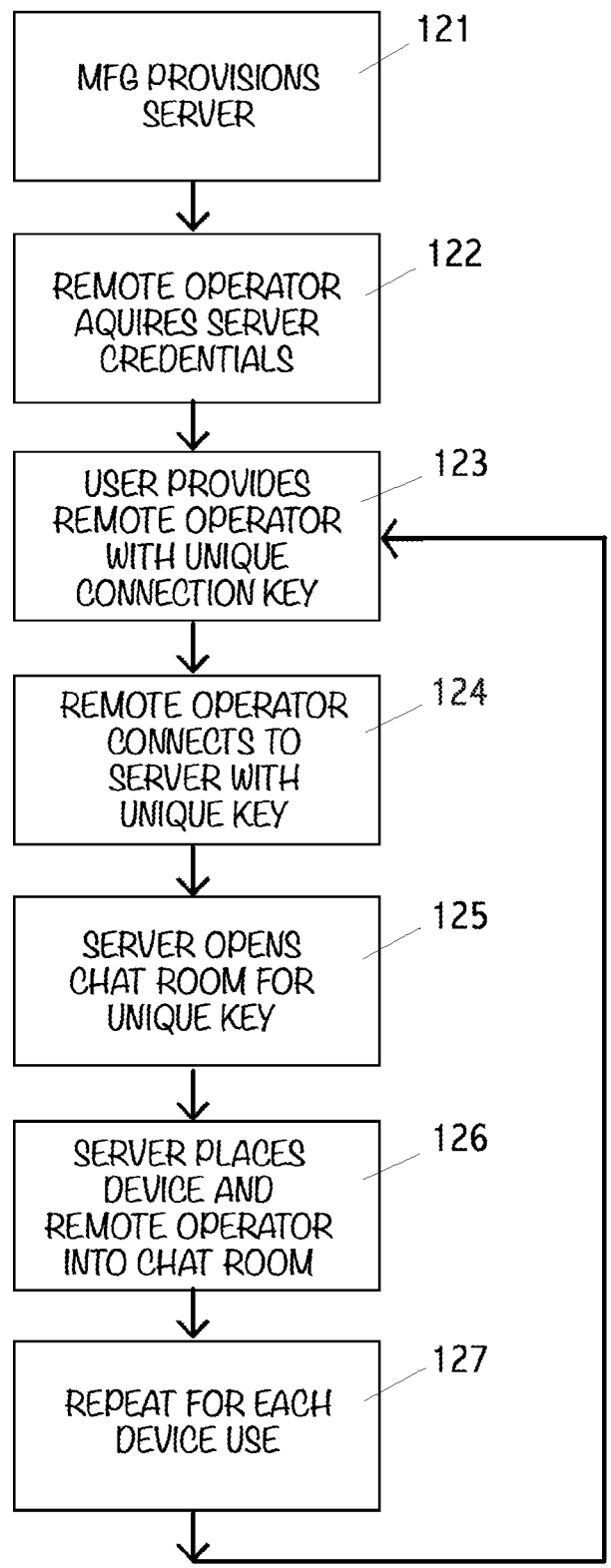
FIG. 12 shows a method of connecting devices with remote operators.

Turning now to FIG. 12, we see a nexus of embodiments to enable private, anonymous, confidential, secure communication between a user and a user-selected remote operator. First, in step 121, the manufacturer or an entity authorized by the manufacturer, provisions, and then typically operates, a server. Such provisioning may comprise connection of the server to a network accessible by devices and remote operators, such as the internet. Such provisioning may also include software to enable steps discussed elsewhere herein, such as FIG. 12, or to enable a chat room.

In step 122 a remote operator who wishes to provide services to a device user acquires credentials to access the server from step 121. Such credentials may be only a URL or IP address, or may include additional credentials such as a password or digital certificate. Such credentials may be provided in many ways, such as publishing them, such as on a manufacturer's web site. Such credentials may be provided only on request by a potential remote operator, enabling the manufacturer to validate or further enable a remote operator. Such credentials may be provided by a user or only by a user, which limits public knowledge of such credentials, which in turn provides additional assurance against hacking, improper use of such credentials, or loss of user privacy. Steps 121 and 122 may be performed in either order, but the order shown in the Figure is preferred.

In step 123, a user selects one or more remote operators and provides them his unique connection key, associated with his device. Such a remote operator may be a distant wife, for example. A user may provide any number of remote operators with his key. If the user provides no remote operator with his key, then his device is not accessible remotely, even if the user has enabled remote control on his device. For example, devices may have remote control enabled by default, in order to simplify configuration by users and simplify usage.

In step 124, a remote operator with at least one connection key connects to the server from steps 121 and 122. Once connected, the remote operator provides a connection key to the server. Step 124 may be repeated if the remote operator has multiple connection keys. Step 124 permits multiple operators with the same connection key to connect simultaneously, non-simultaneously or independently. The manufacture or the server may or may not know the actual identity of the remote operator. For example, some remote operators may remain anonymous, but then be restricted to chat rooms with only a single remote operator. Some remote operators may be known to the server, for example, by having been issued a digital certificate, electronic ID, or password. Such remote operators may be permitted in chat rooms with more than one remote operator or more than one user, or both. That is, a remote operator may remain anonymous at the discretion of the operator of the server, the manufacturer, or the remote operator.

In steps 125 and 126, the server opens a virtual chat room associated with the unique communication key. A chat room is a virtual environment where the "members" (e.g., a user and one or more remote operators) of the chat room may communicate with each other, but non-members do not have access to listening, transmitting, broadcasting, or reading meta-data of the chat room members, chat room communications, or the communication keys. The server opens a chat room uniquely associated with a communication key typically when contacted by either user or remote operator providing that key. A chat room may be closed at the discretion of the server. Users or remote operators have the option of not transmitting or not receiving chat room communications. In some embodiments, a user or remote operator may specifically request that the chat room be closed. In some embodiments, chat rooms are always open or available once a unique key is generated (or following another step), such as after step 91 in FIG. 11. Communications in a chat room may be simple or complex. Some embodiments of this invention do not restrict type or content of communications, while other embodiments may have strict rules regarding type, content, rate or frequency of communications. In a simple embodiment remote operators transmit to the chat room operating commands to the device such as speed or stroke length; while users listen only and do not transmit to the chat room. In more complex embodiments, communications may include audio or video, may involve two-way or multiple-way communications, and may include multiple communication protocols, as known in the art. Embodiments of communications between users and remote operators may include validation or additional identifying information.

Step 127 identifies that steps shown in FIG. 12 may be repeated as necessary. Although the Figure shows repeat from by step 127 to step 123, repetition may include any steps 121 through 126. In one embodiment step 121 is performed once per server; step 122 is performed once per remote operator. In addition, embodiments may repeat from intervening steps 122 through 126. Step 123 may be performed once per user or once per remote operator; it is typically performed each time a user wishes to enable a particular remote operator. If a user wishes to disable a remote operator, one method is for the user to update his connection key, such as described in step 143 in FIG. 14; and then not provide the new connection key to that remote operator.

Figure 13:
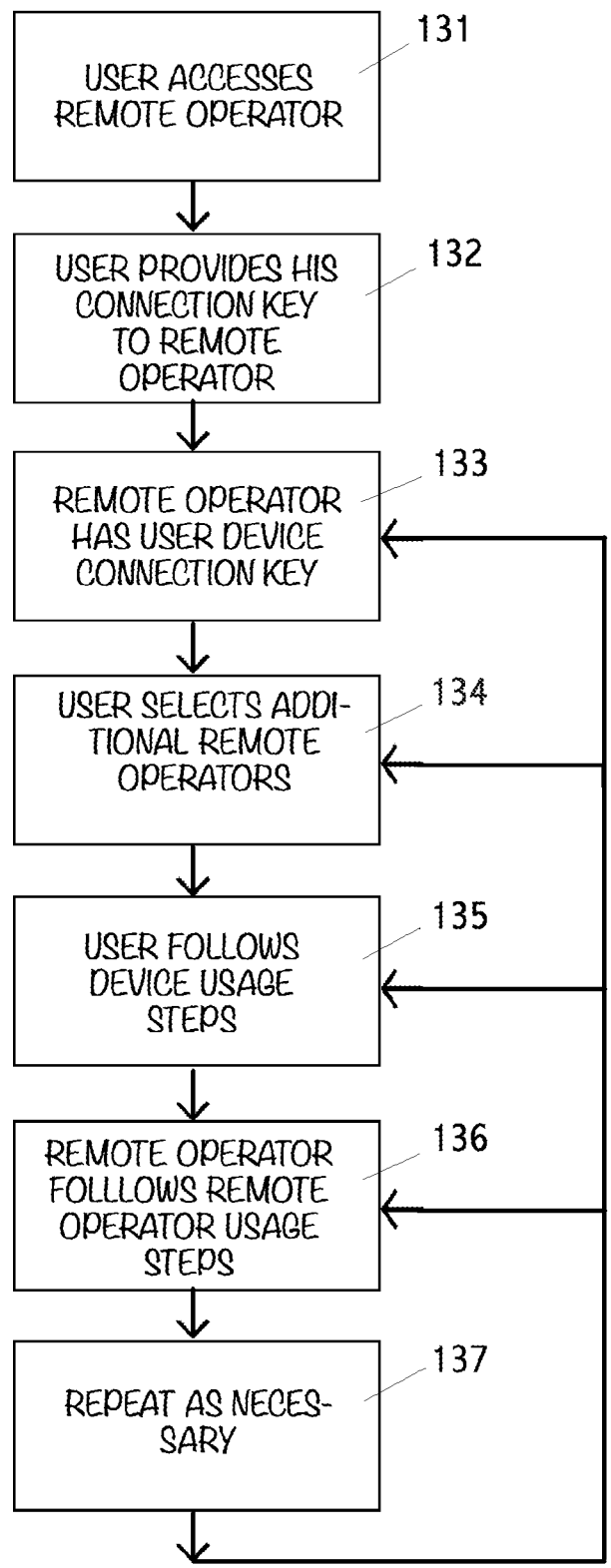
FIG. 13 shows a method of remote operator operation.

Turning now to FIG. 13, we see steps a user performs to use his device anonymously with remote access. Such steps are a nexus of embodiments. In steps 121 and 132 a user selects a remote operator and enables that remote operator to control his device by providing that remote operator with his device connection key. Access to a selected remote operator may be manual, such a by use of a phone call; or electronic, such as by use of an email or https connection; or mediated by a third party. Although, use of a third party potentially reduces or eliminates privacy, anonymity, confidentiality or protection from hacking. As result of step 132, in step 133 a selected remote operator is in possession of the user's unique connection key. In step 134 a user may optionally select additional remote operators, or new remote operators, and then steps 132 and 133 are repeated for each such selection.

In step 135 a user uses his device, as described elsewhere herein. If and when remote operation is enabled, functionality of the device, such as but not restricted to stroke length and speed, may be controlled by the remote operator. In one embodiment the user may turn on or off remote operation during use, such as by a button on the device. A novel advantage of this embodiment is that such a change does not require a user to discontinue device operation or use. As one example, remote operators may keep a chat room open at all times. In this example, a user may connect to his selected remote operators at any time simply by activating a button on his device. Other methods of enabling remote access include voice activation. In some embodiments, remote operation is always enabled. In some embodiments, enablement of remote operation may be controlled by another device. For example, an app on a smart phone may enable or disable remote operation. However, use of such an additional device may compromise security or confidentiality. In one embodiment, two or more devices may act or also act as remote operators. For example, a user-controlled operation of a first device may remotely control operation of a second device. Use of a device as a remote operator is specifically claimed as an embodiment.

In step 136 a selected remote operator follows remote operator usage steps as described elsewhere herein. Note that certain details of implementation of any element or any step in a claim, description, or Figure, may require normal skill of one trained in the art.

In step 137 we see that steps within FIG. 14 may be repeated as necessary. For example, each further time a user wishes to use his device with the same remote operator, such usage may start with step 135.

Turning now to FIG. 14, we see embodiment for a user to create or change his unique device connection key. In Step 141 the user enables device programming. This may be the same method or a different method as enabling remote access for use. For example, the user may hold down a remote access button for a period of time longer than the depressed time required for usage remote access. In step 142, the user programs his device with credentials to access his local network, such as a home Wi-Fi, or hotel Wi-Fi network. In one embodiment, the device creates its own access point and hosts a web browser. In this embodiment, the user uses a standard web browser on a network (e.g., Wi-Fi) enabled device, such as a smart phone, tablet, PC, or voice-activated assistant. Note that reasonable security is available because step 141 is performed typically only once and for a short period of time. Credentials for such access may be provide with a device, or publicly available. They may be unique for a device, or group of devices, or all devices.

In Step 143, a user may optionally change his connection key. Such a change may be needed or desirable because a device is not pre-programmed with a unique connection key; or a user wishes to have a shorter or longer connection key; or a user wishes to disable a previously enabled remote operator from remotely operating his device; or a user believes his connection key has been compromised. One possible compromise is for a first remote operator to provide a second remote operator with the user's connection key. New connections keys may be generated by a user or generated electronically, such as by an app or key or password generator. Typically, a preferred embodiment is for electronic key generation, as users tend to choose easily hacked keys, such as their own name or the name of an intimate partner.

Step 144 is typically performed after any step 143.

Step 145 may be performed manually by the user or automatically, similar to step 123 in FIG. 12. The user may update existing remote operators or new remote operators, in any combination.

In step 146, a server opens a chat room with the new connection key, under conditions described elsewhere herein, such as step 125 in FIG. 12, or the first time either a user or a remote operator connects to the server with the new key from step 144.

Step 147 teaches that steps in FIG. 14 may be repeated as necessary. Typically, repeat operation starts with step 141. In some scenarios, repeat operation may start with step 145. In some embodiments, repeat operation may start with step 146 as the server may have closed a previous chat room and needs to re-open the chat room or open a new chat room.

Although terms like "access point," "Wi-Fi," "internet" and "IP address" are used herein, these terms are construed, including device identification and communication encryption and security, to include terminology for other networks and other wireless protocols such as Bluetooth, Bluetooth Low Energy (BLE) and cellular data protocols such as "4G" and "5G."

Although embodiments are free of a smart phone and free of devices that require downloaded apps, such devices may be used in other embodiments. In particular, devices like the Wi-Fi access point 64 and the user interface device 83 may be replaced, in part or fully, in any combination by such a smart phone, tablet, smart watch or similar device. A downloaded app may be provided by the remote server 85, which protects the patient from provided identifying or usage data to third parties, including to a remote operation point such as 86.

Note also that costs, fees, tokens, coupons, vouchers, blockchain identifiers, and other value represented by digital information, may be provide by, provided to, stored, or otherwise managed by the server 85. Again, this architecture protects the patient from provided identifying or usage data to third parties.

Many descriptions, scenarios, figures, and claims refer explicitly to network architectures and physical devices, not to business models or methods or organizing human behavior, including not to human interaction or human services provided between a patient 81 and a remote operation point 86. However, "methods of treatment" are included in some embodiments and are so claimed embodiments.

Note the following features of embodiments. Smooth external surface of the shell, including connection from the curved distal end to the body of the shell; single slot; lead screw is internal to the shell; sleeve retainer and sleeve are external to the shell; slider has a portion internal to the shell and a portion external to the shell; the slider passes through a slot in the shell; the outside of the shell has a concave recess; operational buttons are located in the distal half of the shell; operational buttons are located in the concave recess. In some embodiments, the slider comprises one, two or more slots through which a sleeve retention strap may pass. Note that the slider moves the entire sleeve, as compared with driving a separate sleeve jacket that moves along the outside of a sleeve. Note that in use, the sleeve moves along the shaft of the patient's penis, as compared to a sleeve that remains in a fixed position on the patient's penis. Note that the entire embodiment comprises only three separable components: the shell, the sleeve, and a sleeve retention strap. In some embodiments, the sleeve retention strap is affixed to either the slider or the sleeve.

Internal to the shell is a power supply to supply internal electronics. Internal electronics including a motor driver, optional programmable processor with non-transitory memory, wireless communication electronics, such as Wi-Fi, interface to optional buttons and optional lights. The motor may be a brushless motor. It may comprise or be proximal to one or more motor sensors, such as magnetic or Hall effect sensors, that detect motor motion, which may be used, in conjunction with the electronics, to count rotations of the lead screw, which in turn may be used to determine the location on the lead screw of the slider. A motor current sensor may be used. See also FIG. 2 for additional views of components.

Embodiments comprise sensors that may be adapted to provide redundant detection of slider location on the lead screw, and to provide additional device safety, reliability, features and convenience. Motor sense sensors may be used, as described to determine the location of the slider via counting rotations of the lead screw. End-of-travel sensors may be used to detect when the slider has reached an effective or desired, predetermined location at the proximal or distal end of the lead screw. In addition, one or more motor current sensors may be used to determine when the motor is drawing excess current, such as the slider having reached a mechanical stop. Thus, with more than one way to detect slider position and slider end points, reliable operation of the device is assured. In addition, redundancy is achieved by using both motor current and the motor sensors to determine the effective speed of the rotation of the lead screw, and thus the effective speed of the slider. In addition, the use of a motor current sensor with other sensors can determine if the slide is jammed, overloaded, or otherwise outside of its intended operation. This, then, provides the ability to change operation, such as slowing down, or fix a jam by reversing the motor, warn the patient, or shut off. Such redundancy and features permit reliable, predictable, safe operation, not available in prior art. Detection of slider position separate from fixed end-point detection permits selectable stroke length and dynamically selectable starting and ending points. Motor sensors may be but are not limited to magnetic or Hall effect sensors. End-of-motion sensors for detecting slider position may be but are not limited to infrared (IR) or another optical sensor. They may alternatively be magnetic or Hall effect sensors, detecting, for example, a piece of metal or magnet affixed to the slider, or detecting the lead screw nut. One or more sensors may be affixed, such as by soldering, to an electronic circuit board, and thus not requiring separate assembly and wiring of the sensor to the electronic circuit board.

Push rods, such as made out of plastic or metal, may be used to communicate motion of a button on the shell to a switch on the electronic circuit board. Light pipes, such as made out of transparent plastic, may be used to transmit light from an optical device, such as an LED, on the electronic circuit board, to a display point on the shell.

A variety of plastics and rubbers are suitable materials for the shell. A "soft touch" material, layer, coating of paint may be used over all or a portion of a hard plastic shell to improve grip and tactile feel of the shell.

A sleeve may be made out of many different materials. Typically, such materials should be flexible, comfortable, and washable. Single use sleeves may be used. Sleeves may be offered in different diameters, different lengths, different materials, different colors, and with different interior texturing. Typical use includes a personal lubricant, supplied by the patient, on the inside of the sleeve. Different types of sleeve material have different compatibility with different types of lubricants. For example, silicone is a preferred material, but may not be compatible with silicone-based lubricants. Latex is another preferred material, but some patients may be allergic to latex. Patients may have a preference for a sleeve that is transparent, lightly colored, or brightly colored. Patients may have a preference for different texturing on the inside of the sleeve.

In one embodiment, the outside of the shell comprises a smooth concave portion. The concave portion may be shaped such that a cross-section at or near the middle of the shell has a concave section of the circular or elliptical cross-section, while a similar cross-section at or near the ends of the shell has no concave portion, and is thus predominantly circular or elliptical. See also Figures. Such a concave portion aids in the ergonomic handling of the device and recesses the buttons against accidental use or damage.

Suitable dimensions for the length of the shell are in the range of 120 mm to 400 mm long, not counting the slider or sleeve. Another suitable range is from 185 mm to 280 mm. Yet another suitable range is 220 mm to 240 mm. Suitable dimensions for the diameter of the outside of the shell are in the range of 25 to 150 mm. Another suitable range is 50 mm 100 mm. Yet another suitable range is 60 mm to 80 mm. A suitable material for the shell is acrylonitrile butadiene styrene (ABS). A suitable material for the slider is polyoxymethylene (POM). A guide rod may be coated with titanium nitride or a similar, low-friction, material. Alternatively, low-friction material may be used such as polytetrafluoroethylene (PTFE) for the slider, the guide rods, or as a coating or intermediate material or element.

A suitable component for an IR sensor is Everlight (EVERLIGHT ELECTRONICS CO., LTD., No. 6-8, Zhonghua Rd., Shulin Dist., New Taipei City 23860 Taiwan) model ITR8307. A suitable module for providing a processor and communications is ESP32-WROOM-32D, from Espressif Systems (#101, Block 2, 690 Bibo Road, Zhangjiang High-Tech Park, Pudong, Shanghai, China 201203). A suitable motor driver is Allegro A4931, from Allegro Microsystems, LLC (955 Perimeter Road, Manchester, N.H. 03103).

Suitable outside diameter of the sleeve is 55 mm, plus or minus 30%, or plus or minus 15%, or plus or minus 5%. Suitable diameter of a sleeve opening at its proximal end is 22 mm, plus or minus 30%, or plus or minus 15%, or plus or minus 5%.

A suitable motor is a 50 mm long brushless motor, with integral shaft or current sensors, described elsewhere herein, with a 12,000 RPM peak rotational speed. A suitable lead screw has an 8 mm lead, 2 mm pitch and 8 mm diameter.

Embodiments are free of, in any combination: a brushed motor; a stepper motor; an eccentric driven weight; two or more motors; batteries, or smart phone app. Indeed, since embodiments communicate directly with a patient's wireless router, modem, or similar interface to a community network (e.g., the internet), no intermediate electronics, such as a smart phone, is required for operation involving a remote device or person. Such a feature is important to preserve privacy. Embodiments use only a single motor, which may be brushless. Although embodiments are free of a discreet vibrator, embodiments may use a single motor, operated in such as way, as to mimic vibration.

Other embodiments may include batteries, voice input, interfaces to electronic voice-activated, digital assistant, consumer control devices such as "Siri®" or "Alexa®." trademarks of Apple (One Infinite Loop, Cupertino, Calif.) and Amazon (410 Terry Ave. North, Seattle, Wash.), respectively; audio output; two-way voice communication with a remote operation point; speed control buttons; and operating sequence selection buttons. Other embodiments may include interfaces to read smart cards, memory storage devices, near-field communication (NFC) devices, wireless charging devices, optical interface (similar to those commonly used in consumer remote control devices, such as for TVs), or a fingerprint reader.

Yet another embodiment includes one or more controllable light sources positioned to illuminate the sleeve in operation. Such a light source may in the interior of the shell and shine through the slot, or may be located on the outside of the shell.

A novel feature of embodiments is their capability to connect to a remote operation point. Such a remote operation point might be or might comprise, for example, a remote partner to provide intimacy with a remote partner, doctor or therapist. Or, the remote operation point may comprise an electronic device or software, in combination, to mimic intimacy, which might comprise a video game or surrogate, or provide entertainment or a medical service. In various embodiments, or various selectable operational features, such a remote operation point may include the ability to control the device operation, observe device operation, or synchronize operation with an electronic device, including mechanical, audio or visual devices. In some embodiments, the remote operation point may be nearby, such as in the same room, or may be located anywhere in the world, such as by internet or other network connectivity. A remote operation point may comprise a similar or non-similar intimacy or sexual stimulation device, video game, video display, audio input, audio output, voice input, voice output. Control information may flow in either direction. Consider, for example, two similar devices. A patient of one device configures his device to a preferred operation, which then automatically drives or configures a remote device or a remote operation point to perform synchronized, or non-synchronized by similarly. This may be viewed as a master-slave relationship of device operation. Any device may operate as either the master of the slave. In another embodiment scenario, actions within a video game or video display may be synchronized with the device. Embodiments are specifically claimed for such connectivity features.

Another novel feature of the embodiments using remote connectivity is that they are free of patient-identifying information, or are free of any registration requirement of a patient, or are free of requirement for a smart phone app, in any combination. The server operates as an intermediate communication node between an embodiment and one or more remote operation points. The server maintains a database linking a device ID to a network address. In this way, a person or device at a remote operation point need enter only such a device ID to connect to an embodiment. This preserves the privacy of a patient with the embodiment and the remote operation point. That is, no personal information needs to be kept, such as is required to download a smartphone app. Embodiments are free of holding, requesting, or requiring personal identifying information. Embodiments are free of requiring, storing or using a network ID, such as an IP address (or similar) of a network endpoint, for connectivity between an embodiment and a remote operation point. Any required network addresses are stored in the server, rather than in a device, local smart phone app, or local digital assistant. Each endpoint, such as an embodiment or a remote operation point communicates directly with the server, whose network ID or equivalent is known to the endpoint. Such a server network ID may be included in an embodiment as manufactured, configured or sold. In some embodiments, a patient is never prompted and is not required to enter a server network ID. One benefit of such an embodiment is patient privacy. Another benefit is easier and faster setup. Another benefit is that no smart phone or similar device is required. Typically, a one-time setup is required to connect to a local Wi-Fi or other local network access point, if connection to a remote operation point is desired. If no such connectivity is desired, then no such patient setup is required. The server supports one-to-many, many-to-one, and many-to-many connectivity. For example, a single software treatment regimen, operating as the remote operation points, may connect to a plurality of patient devices. As another example, one patient may connect to multiple remote operation points, such as one remote operation point performing a control function and another remote operation point may perform only observationally. Yet another example is the use of multiple patients or users operating in a coordinated fashion, such as a multi-player game.

Yet another novel feature of embodiments is the inclusion of an "API," "library," or "framework," that permits third party developers to add features to a device of connectivity features, or features for a remote operation point. For example, a video game, video display, or voice input/output, or connectivity or synchronization with third party devices, software or media. A benefit of the combination of such third-party products and the above-described use of a server is that no patient-identifying information is required or is provided to such a third-party developer. In some embodiment, a patient using non-traceable monetary equivalents, such as gift cards, block-chain codes, and the like, may purchase features. Such non-traceable monetary equivalents may be bundled into a device, as sold or configured. Such embodiments are specifically claimed. Some embodiments are able to read a separate memory device such as a smart card, USB stick, or similar device. An electronic connector, Near Field Communication (NFC), or similar technology may be used for this purpose. Such a memory device may contain device IDs, or tokens for purchasing remote services or remote or local capabilities, or firmware or software updates.

In yet another embodiment, the server compensates for communication delay between the first device and the server, or the remote operation point and the server, or both, such that real-time synchronization between the first device and the remote operation point is achieved or preserved. For example, time stamps may be adjusted as they pass through the server, or delay of a communication packet or message may be used, in conjunction with the speed of operation of the first device, so as to maintain a synchronized phase relationship between repetitive motion of the slider in the first device and associated motion, displayed or physical, or both, at the remote operation point.

For claimed embodiments below, see also claim text for terminology, such as "first device," "remote operating point," and "server," among others.

Although a complex, novel system the enables personal intimacy between two people, remote from each other, may be viewed as a form of "organizing human behavior," which in the legal regime as of the filing date, is not considered a "useful art," as stated by the US Constitution in Article 1 Section 8 Clause 8; nonetheless specific embodiments of enabling or assisting in such personal intimacy are claimed.

Although a complex, novel system the enables synchronization of mechanical motion of masturbation with elements of a video game or video display may be viewed as a form of "organizing human behavior," which in the legal regime as of the filing date, is not considered a "useful art," as stated by the US Constitution in Article 1 Section 8 Clause 8; nonetheless specific embodiments assisting in such synchronization are claimed, including such a video game and associated elements in the video game or video display, and including motions of synchronized characters in the video game or video display.

Such embodiments may comprise elements in any combination: transmission from a remote operation point to first device: a desired speed of the first device; a desired position of the slider of the first device; a time stamp of a desired location of the slider on the lead screw; such that either the speed of motion of a character in a video game or video display is synchronized with a speed of motion of the slider of the first device, or location of motion of a character in a video game or video display is synchronized with a location of the slider on the lead screw of the first device, wherein the control electronics in the first device adjusts either the speed of motion of the slider on the lead screw or the position of the slider on the lead screw, or both, to achieve such synchronization.

Such embodiments may comprise elements in any combination: audio output associated with a character in a video game or video display transmitted as digital audio information over the network, through the server to the first device, playing from audio output of the first device, or playing from audio output of an audio device associated with the first device and proximal to the first device.

Such embodiments may comprise elements in any combination: vocalizations of a patient of the first device or local sounds received by the first device, transmitted as digital audio through the server to a remote operating point, vocalized by a character in a video game or a character in a video display.

Such embodiments may comprise elements in any combination: two or more separate patient, each with his own first device; connected via the server to a single video game or video display, wherein the single video game or video display may be played or viewed by more than one person, wherein the single video game of video display has two or more characters, each such character associated with a patient, and wherein the embodiment comprises any combination of embodiments described above or elsewhere herein, in claims or drawings, such as synchronized motion or synchronized audio between each patient and the patient's associated character.

Although some claims are directed to a device comprising both a shell and a sleeve, embodiments are specifically claimed for the shell only, without a sleeve. Embodiments are specifically claimed for a device comprising batteries, either primary or rechargeable, and free of a power cord required for operation. Embodiments are claimed wherein the device uses exactly one motor. Embodiments are claimed wherein the device is free of a mechanical vibrator. Embodiments are claimed wherein the device is adapted such that when the motor rotates the lead screw, the sleeve retainer portion of the slider is driven coaxial, via the slider. Embodiments are claimed where the remote operator causes the user device to synchronize with either video or audio, which video or audio may or may originate at the remote operator. Embodiments claimed include replacing one or more buttons with a voice-activated input and optionally voice or audio output. A motor may be a linear or rotating motor. If a motor is linear, a lead screw may not be required for the motor to drive the slider. In some embodiments one or more guide rods may be part of or affixed to the shell. Guide rods are not necessarily circular in cross-section. A guide rod may be a recess, wherein the slider rides within the recess.

Definitions

"app"—An application on smart phone, as this term is commonly used. May also be called a "downloadable application."

"co-axial"—Parallel to an axis.

"electronic user interface device"—a device such as a personal computer, tablet, and the like, that may run a web browser or similar software. It may also include devices such as a smart phone, smart watch or voice- or motion-sensitive device such as a personal assistant. Note that some embodiments are free of any device that may transmit personal or personal identifying information.

"patient"—a person wearing and using the device, also referred to a as a "user."

"remote operation point"—also called a "remote operator" or "remote device operator." The term that describes a terminal end of communication to or from the device. The remote operation point may comprise a caregiver, such a doctor, nurse, surrogate, or other medical practitioner. It may be an intimate partner of the patient. It may be a non-human device, such as medical program, video game, video, audio, or electronic or adult entertainment. The phrases, "remote caregiver" and "remote device" refer to any remote operation point, unless otherwise clear from the context. Note that in some usage scenarios, the remote operation point is not far from the device, such as in the same room or same physical facility.

"server"— a programmable device, such as a computer, which may be remote from any patients; users; remote operation points; whether human or machine, typically connected to other servers, communication hardware, storage devices, or end-user devices; typically whose primary purpose is not to provide a user interface, but rather to provide functionality to any such other connected devices. Servers may be located anywhere, and have any physical form, include distributed. A server does not need to be remote.

"shell"— A component that encloses (partially or fully) primary mechanical and electrical components. This may be viewed as a "body" of an embodiment, as this term is sometimes used in the art, although in an alternative construction the term, "body," includes components interior to the shell.

"smart phone"—or any other user-oriented or personal "smart device," including tablets, watches, laptops, electronic assistants, and the like.

"third party"—a device, person or service who is connected to the server but is neither the patient/device nor the remote operation point.

Ideal, Ideally, Optimum and Preferred—Use of the words, "ideal," "ideally," "optimum," "optimum," "should" and "preferred," when used in the context of describing this invention, refer specifically a best mode for one or more embodiments for one or more applications of this invention. Such best modes are non-limiting, and may not be the best mode for all embodiments, applications, or implementation technologies, as one trained in the art will appreciate.

All examples are sample embodiments. In particular, the phrase "invention" should be interpreted under all conditions to mean, "an embodiment of this invention." Examples, scenarios, and drawings are non-limiting. The only limitations of this invention are in the claims.

May, Could, Option, Mode, Alternative and Feature—Use of the words, "may," "could," "option," "optional," "mode," "alternative," "typical," "ideal," and "feature," when used in the context of describing this invention, refer specifically to various embodiments of this invention. Described benefits refer only to those embodiments that provide that benefit. All descriptions herein are non-limiting, as one trained in the art appreciates. Embodiments of this invention explicitly include all combinations and sub-combinations of all features, elements and limitation of all claims. Embodiments of this invention explicitly include all combinations and subcombinations of all features, elements, examples, embodiments, tables, values, ranges, and drawings in the specification and drawings. Embodiments of this invention explicitly include devices and systems to implement any combination of all methods described in the claims, specification and drawings. Embodiments of the methods of invention explicitly include all combinations of dependent method claim steps, in any functional order. Embodiments of the methods of invention explicitly include, when referencing any device claim, a substation thereof to any and all other device claims, including all combinations of elements in device claims. Claims for devices and systems may be restricted to perform only the methods of embodiments or claims.

We claim:

1. A method of connecting a user device anonymously to a remote operator comprising the steps:

provisioning a server, comprising the sub-steps:
(a) creating a device-unique connection key;
(b) programming the connection key into the user device;
(c) providing a user of the user device with the connection key;
(d) programming a device-access credential set into the user device;
(e) programming a user-to-server-access credential set into the user device;

opening a server chat room associated with the connection key, comprising the sub-steps:
(f) providing the remote operator with a remote-operator-to-server-access credential set;
(g) providing to the remote operator, by the user, the connection key;
(h) accessing the server chat room, by the user, using the connection key and the user-to-server-access credential set;
(i) accessing the server chat room, by the remote operator, using the connection key and the remote-operator-to-server-access credential set;
(j) associating the server chat room with the connection key;
(k) providing communication between the user device and the remote operator, via the server chat room; wherein other user devices, not having the connection key, and other remote operators, not having the connection key, are blocked from communicating via the server chat room;

using the user device by the user anonymously, comprising the sub-steps:
(l) enabling, by the user, the user device for remote access; and
(m) controlling, by the remote operator, the user device, via communication between the remote operator, through the server chat room, and the user device.

2. The method of claim 1 further comprising the additional step:
(n) closing the server chat room associated with the connection key;
wherein the connection key is not stored in the server during a time when the server chat room is closed.

3. The method of claim 2 wherein:
during the time when the chat room is closed, the connection key is stored only in the user device and in other devices or other remote operators provided, by the user, directly or indirectly, with the connection key.

4. The method of claim 1 wherein:
the method is free of a requirement for the user to download a computer application.

5. The method of claim 1 wherein:
the remote operator, the server, the server chat room and a device manufacturer are all free of any information that identifies personally the user of the user device.

6. The method of claim 1 comprising the additional step:
(o) synchronizing, controlled by the remote operator, a user device motion with a video stream.

* * * * *